United States Patent
Coates et al.

[11] Patent Number: 5,942,648
[45] Date of Patent: Aug. 24, 1999

[54] NAPHTHALENE DERIVATIVES

[75] Inventors: David Coates, Wimborne; Mark Goulding; Simon Greenfield, both of Poole, all of United Kingdom; Volker Reiffenrath, Rossdorf, Germany; Reinhard Hittich, Modautal, Germany; Herbert Plach, Darmstadt, Germany

[73] Assignee: Merck Patent Gesellschaft mit beschränkter Haftung, Germany

[21] Appl. No.: 08/811,179

[22] Filed: Mar. 4, 1997

Related U.S. Application Data

[63] Continuation of application No. 08/462,322, Jun. 5, 1995, abandoned, which is a continuation of application No. 08/139,127, Oct. 21, 1993, abandoned.

[30] Foreign Application Priority Data

Oct. 22, 1992 [GB] United Kingdom ............... 9222178

[51] Int. Cl.$^6$ ............................................... C07C 15/24
[52] U.S. Cl. ......................... 585/26; 585/24; 585/25; 585/27; 558/411; 558/425; 560/100; 560/139; 560/259; 568/56; 568/58; 568/328; 568/659; 568/661
[58] Field of Search ..................... 585/24, 25, 26, 585/27; 558/411, 425; 560/100, 139, 259; 568/56, 58, 328, 659, 661

[56] References Cited

U.S. PATENT DOCUMENTS 4,261,651  4/1981  Gray et al. ........................ 350/350 R (List continued on next page.)

FOREIGN PATENT DOCUMENTS 6137742  2/1986  Japan .

(List continued on next page.)

OTHER PUBLICATIONS

Chem Abstracts: 105: 105906q (1986).

(List continued on next page.)

*Primary Examiner*—Ponnathapura Achutamurthy
*Attorney, Agent, or Firm*—Millen, White, Zelano, & Branigan, P.C.

[57] ABSTRACT

Naphthalene derivatives of the fomula I

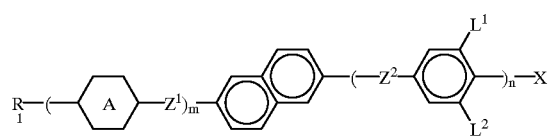

in which:

$R^1$ is an alkyl or alkenyl radical which is unsubstituted, monosubstituted by CN or $CF_3$ or monosubstituted by halogen and has 1 to 15 carbon atoms, it also being possible for one or more $CH_2$ groups in these radicals to be replaced, in each case independently of one another, by —O—, —S—,

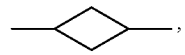

—CO—, —CO—O—, —O—CO— or —O—CO—O— in such a manner that oxygen atoms are not linked directly to one another,

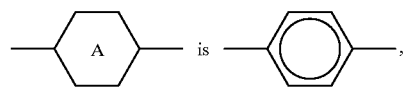

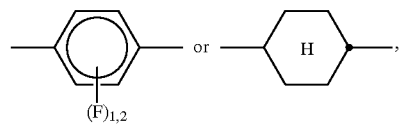

m is 0, 1 or 2, n is 0 or 1, where m+n is 1 or 2, $Z^1$ and $Z^2$ are each, independently of one another, —$CH_2CH_2$—, —C≡C— or a single bond, $L^1$ and $L^2$ independently of one another, are H or F, x is an alkyl or alkoxy radical which is unsubstituted, monosubstituted by CN or $CF_3$ or substituted bi halogen and has 1 to 15 carbon atoms, or is OH, CN, SCN, OCN, NCS or Q—Y, where Q is a single bond, $(CF_2)_r$ or $O(CF_2)_r$, r is 1 or 2, and Y is H, F, Cl or Br, with the provisos that a) in the case where m=0, $Z^2$=a single bond, n=1 and x=CH $CF_3$ or SCN, $L^1$ is F, b) in the case where m=0, $Z^2$=a single bond, n=1 and X=alkyl, alkoxy or F a $L^1$ and $L^2$ are identical and are F.

4 Claims, No Drawings

U.S. PATENT DOCUMENTS

| | | | |
|---|---|---|---|
| 4,737,297 | 4/1988 | Yoshida et al. | 252/9 |
| 4,800,032 | 1/1989 | Murphy | 252/51.5 A |
| 5,252,253 | 10/1993 | Gray et al. | 252/299.62 |

FOREIGN PATENT DOCUMENTS

| | | |
|---|---|---|
| 2 227 019 | 7/1990 | United Kingdom . |
| 2 238 309 | 5/1991 | United Kingdom . |
| 2 244 710 | 12/1991 | United Kingdom . |

OTHER PUBLICATIONS

Chem Abstracts: 114: 33611a (1991).

Chem Abstracts: 118: 202214p (1993).

Chem Abstracts: 118: 244,729v (1993).

Chem Abstracts: 120: 335203x (1994).

Gray et al., "Synthesis and Propertise of Some 2–n–Alkyl–6–(4'–cyanophenyl)–naphthalenes, etc." Mol. Cryst. Liq. Crystal. 1983, pp. 123–138.

NAPHTHALENE DERIVATIVES

This application is a continuation of application Ser. No. 08/462,322, filed Jun. 5, 1995, which is a continuation of application Ser. No. 08/139,127 filed Oct. 21, 1993, now abandoned.

The invention relates to naphthalene derivatives of the formula I

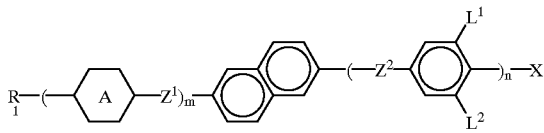

in which $R^1$ is an alkyl or alkenyl radical which is unsubstituted, monosubstituted by CN or $CF_3$ or at least monosubstituted by halogen and has 1 to 15 carbon atoms, it also being possible for one or more $CH_2$ groups in these radicals to be replaced, in each case independently of one another, by —C—, —S—,

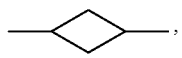

—CO—, —CO—O—, —O—CO— or —O—CO—O— in such a manner that oxygen atoms are not linked directly to one another,

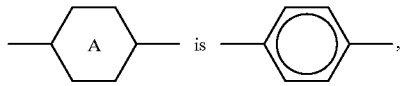

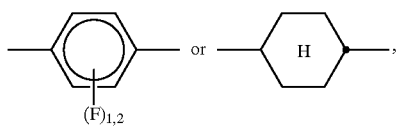

m is 0, 1 or 2,
n is 0 or 1, where
m+n is 1 or 2,
$Z^1$ and $Z^2$ are each, independently of one another, —$CH_2CH_2$—, —C≡C— or a single bond,
$L^1$ and $L^2$ independently of one another, are H or F,
X is an alkyl or alkoxy radical which is unsubstituted, monosubstituted by CN or $CF_3$ or at least monosubstituted by halogen and has 1 to 15 carbon atoms, or is OH, CN, SCN, OCN, NCS or Q—Y,
where
Q is a single bond, $(CF_2)_r$ or $O(CF_2)_r$,
r is 1 or 2, and
Y is H, F, Cl or Br,
with the provisos that
a) in the case where
m=0, $Z^2$=a single bond, n=1 and X=CN, $CF_3$ or SCN, $L^1$ is F,
b) in the case where
m=0, $Z^2$ a single bond, n=1 and X=alkyl alkoxy or F, $L^1$ and $L^2$ are identical and are F.

The invention furthermore relates to the use of these compounds as components of liquid-crystalline media and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel, stable, liquid-crystalline or mesogenic compounds which are suitable as components of liquid-crystalline media and in particular simultaneously have relatively low viscosity and relatively high dielectric and optical anisotropy.

It has now been found that compounds of the formula I are eminently suitable as components of liquid-crystalline media. In particular, they have relatively low viscosities. They can be used to obtain stable liquid-crystalline media having a broad mesophase range and advantageous values for the optical and dielectric anisotropy.

Liquid crystals of the formula

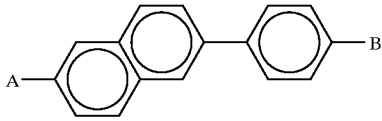

have already been disclosed. Bull. Soco Chim. France (1975), 11–12 (2), 2521, describes compounds of the formulae

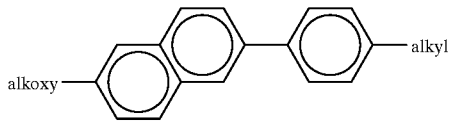

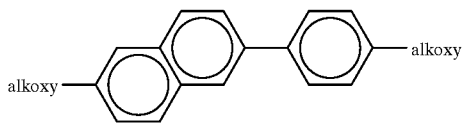

Helv. Chim. Acta 68 (5), 1406–26 (1985), discloses compounds of the following formulae

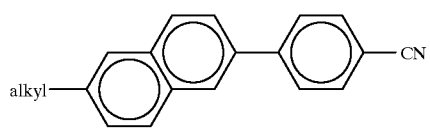

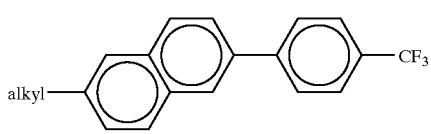

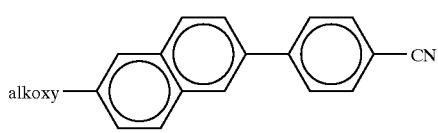

-continued

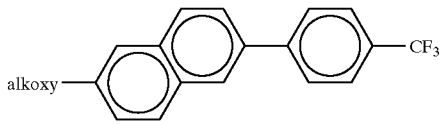

Finally, GB 2,227,019 mentions compounds of the formulae

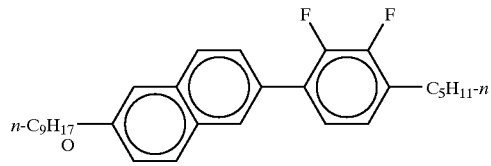

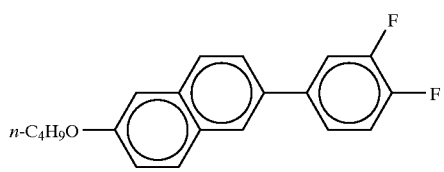

The compounds of the formula I wherein m=0 and n=1 are embraced by the broad formula of the WO 92/16500. But in the whole document there is not disclosed a single compound of the present invention.

However, in view of the very wide variety of areas of application of compounds of this type, it was desirable to have available further compounds which have properties precisely customised to the particular applications.

Compared with the phenylnaphthalene derivatives disclosed hitherto, the compounds according to the invention have a higher $\Delta\epsilon$ and particularly favourable elastic properties The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimise its threshold voltage and/or its viscosity.

Due to their, particularly good stability, the compounds according to the invention are particularly suitable as components of aFT and projection display mixtures.

The compounds of the formula I are in particular suitable as components for liquid crystal media for displays which are based on the principle of polymer dispersed liquid crystals (pdlc) or polymer liquid crystals (pnlc) due to their favorable optical anisotropy and the dielectric anisotropy.

In the pure state, the compounds of the formula are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystalline display elements, in particular electro-optical display elements, which contain media of this type.

For simplicity below, A denotes a radical of the formula

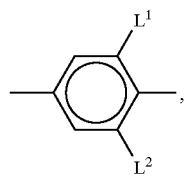

and Nap denotes a naphthalene-2,6-diyl radical, Cyc denotes a 1,4-cyclohexylene radical and Phe denotes a 1,4-phenylene radical, it being possible for Cyc and/or Phe to be unsubstituted or monosubstituted or disubstituted by F or CN.

The compounds of the formula I include, in particular, compounds of the sub-formulae I1 to I57
R-Nap-A-X I1
R-Nap-$Z^2$-X I2
R-Cyc-Nap-A-X I3
R-Cyc-Nap-$Z^2$-X I4
R-Phe-Nap-A-X I5
R-Phe-Nap-$Z^2$-X I6
R-Cyc-$Z^1$-Nap-A-X I7
R-Cyc-$Z^2$-Nap-$Z^2$-X I8
R-Phe-$Z^1$-Nap-A-X I9
R-Phe-$Z^2$-Nap-$Z^2$-X I10
R-Cyc-Cyc-Nap-A-X I11
R-Cyc-Phe-Nap-A-X I12
R-Cyc-$Z^1$-Cyc-Nap-A-X I13
R-Cyc-$Z^1$-Phe-Nap-A-X I14
R-Cyc-Cyc-$Z^1$-Nap-A-X I15
R-Cyc-Cyc-$Z^1$-Nap-$Z^2$-A-X I16
R-Cyc-$Z^1$-Cyc-$Z^1$-Nap-A-X I17
R-Cyc-$Z^1$-Cyc-$Z^1$-Nap-$Z^2$-A-X I18
R-Cyc-Phe-$Z^1$-Nap-A-X I19
R-Cyc-$Z^1$-Phe-$Z^1$-Nap-A-X I20
R-Cyc-Phe-$Z^1$-Nap-$Z^2$-A-X I21
R-Cyc-$Z^1$-Phe-$Z^1$-Nap-$Z^2$-A-X I22
R-Phe-Phe-Nap-A-X I23
R-Phe-$Z^1$-Phe-Nap-A-X I24
R-Phe-$Z^1$-Phe-Nap-$Z^2$-A-X I25
R-Phe-$Z^1$-Phe-Nap-A-X I26
R-Phe-$Z^1$-Phe-$Z^1$-Nap-A-X I27
R-Phe-$Z^1$-Phe-$Z^1$-Nap-$Z^2$-A-X I28
R-Phe-Phe-$Z^1$-Nap-A-X I29
R-Phe-Phe-$Z^1$-Nap-$Z^2$-A-X I30
R-Phe-Cyc-Nap-A-X I31
R-Phe-Cyc-Nap-$Z^2$-A-X I32
R-Phe-$Z^1$-Cyc-Nap-A-X I33
R-Phe-$Z^1$-Cyc-Nap-$Z^2$-A-X I34
R-Phe-Cyc-$Z^1$-Nap-A-X I35
R-Phe-Cyc-$Z^1$-Nap-$Z^2$-A-X I36
R-Phe-$Z^1$-Cyc-$Z^1$-Nap-A-X I37
R-Phe-$Z^1$-Cyc-$Z^1$-Nap-$Z^2$-A-X I38
R-Cyc-Nap-X I39
R-Phe-Nap-X I40
R-Cyc-$Z^1$-Nap-X I41
R-Phe-$Z^1$-Nap-X I42
R-Cyc-Cyc-Nap-X I43
R-Cyc-$Z^1$-Cyc-Nap-X I44
R-Cyc-Cyc-$Z^1$-Nap-X I45
R-Phe-Cyc-Nap-X I46
R-phe-$Z^1$-Cyc-Nap-X I47
R-Phe-$Z^1$-Cyc-$Z^2$-Nap-X I48
R-Phe-Cyc-$Z^1$-Nap-X I49
R-Phe-Phe-Nap-X I50

R-Phe-Z¹-Phe-Nap-X  I51
R-Phe-Z¹-Phe-Z¹-Nap-X  I52
R-Phe-Phe-Z¹-Nap-X  I53
R-Cyc-Phe-Nap-X  I54
R-Cyc-Z¹-Phe-Nap-X  I55
R-Cyc-Z¹-Phe-Z¹-Nap-X  I56
R-Cyc-Phe-Z¹-Nap-X  I57
Some very particularly preferred smaller groups of compounds are those of the subformulae Ia to Iq (L=H or F):
Ia
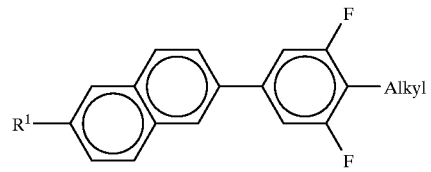
Ib
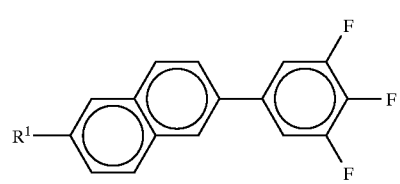
Ic
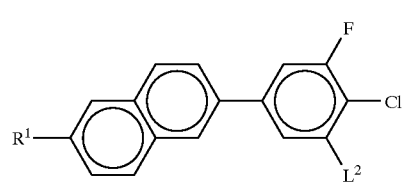
Id
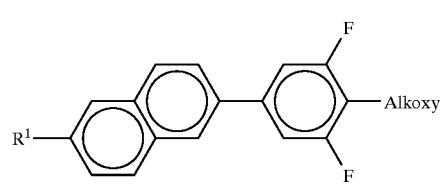
Ie
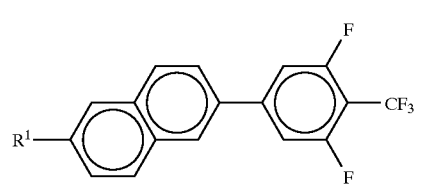
If
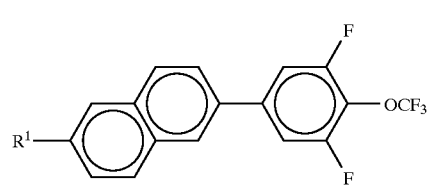
Ig
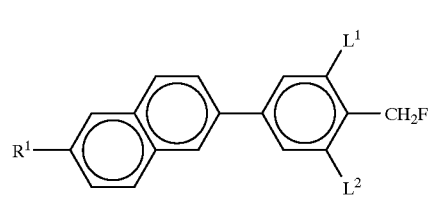
-continued
Ih
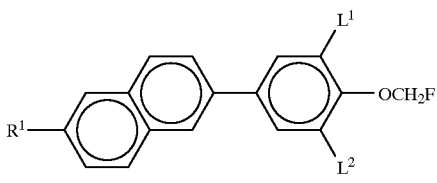
Ii
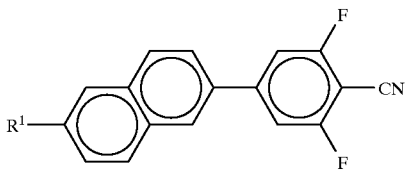
Ij
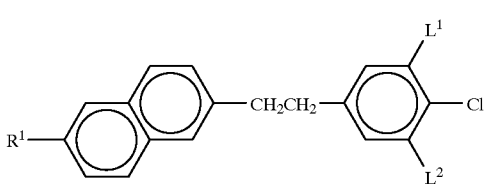
Ik
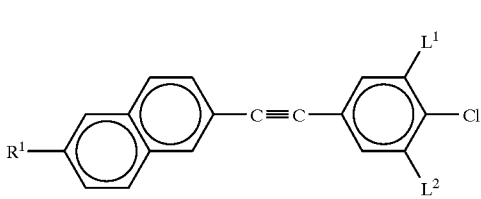
Il
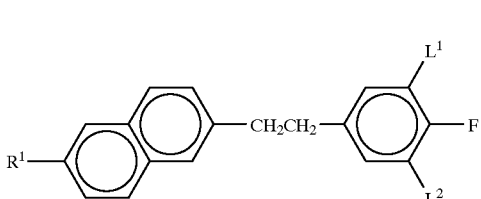
Im
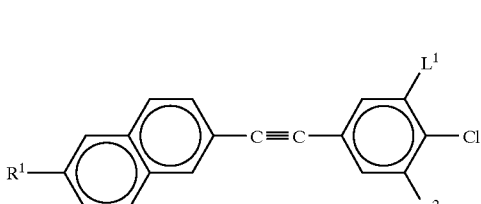
In
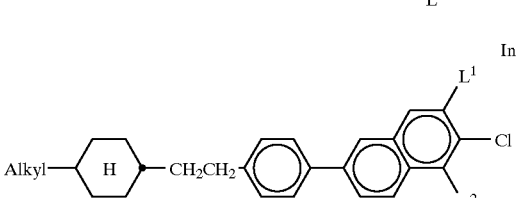
Io
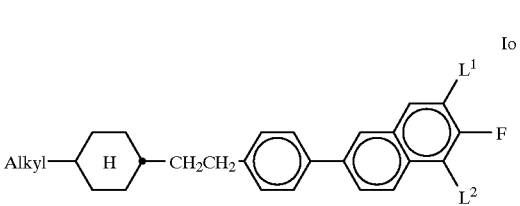

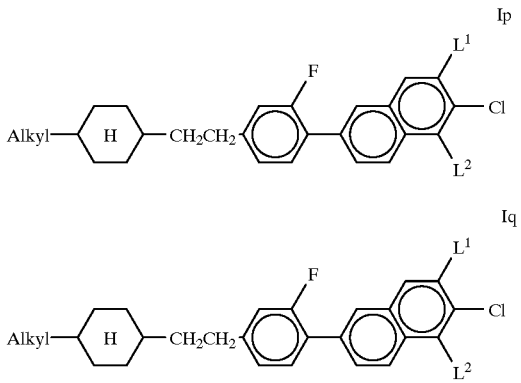

X is preferably F, Cl, $OCF_3$, $CF_3$, $OCH_2CF_3$, $CH_2F$, $CF_2H$, $OCH_2F$, $OCF_2H$, CN, NCS, alkyl or alkoxy.

If $R^1$ is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

Compounds of the formula I containing branched wing groups $R^1$ may occasionally be of importance due to better solubility in the customary liquid-crystalline base materials, but in particular as chiral dopes if they are optically active. Smectic compounds of this type are suitable as components of ferroelectric materials.

Branched groups of this type generally contain not more than one chain branch. Preferred branched radicals $R^1$ are isopropyl, 2-butyl (=1-methylpropyl), isobutyl (=2-methylpropyl)e 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

Compounds of the formula I which contain wing groups $R^1$ which are suitable for polycondensations are suitable for the preparation of liquid-crystalline polycondensates.

The formula I covers, the racemates of these compounds and the optical antipodes, and mixtures thereof.

Of these compounds of the formula I and of the sub-formulae, those are preferred in which at least one of the radicals present therein has one of the preferred meanings indicated.

The compounds of the formula I are prepared by methods known per se, as described in the literature (for example in the standard works such as Houben-Weyl, Methoden der Organischen Chemie [Methods of Organic Chemistry], Georg-Thieme-Verlag), to be precise under reaction conditions which are known and suitable for said reactions Use may also be made here of variants which are known per se, but are not described here in greater detail.

The compounds according to the invention can be prepared, for example, in accordance with the following schemes:

SCHEME 1

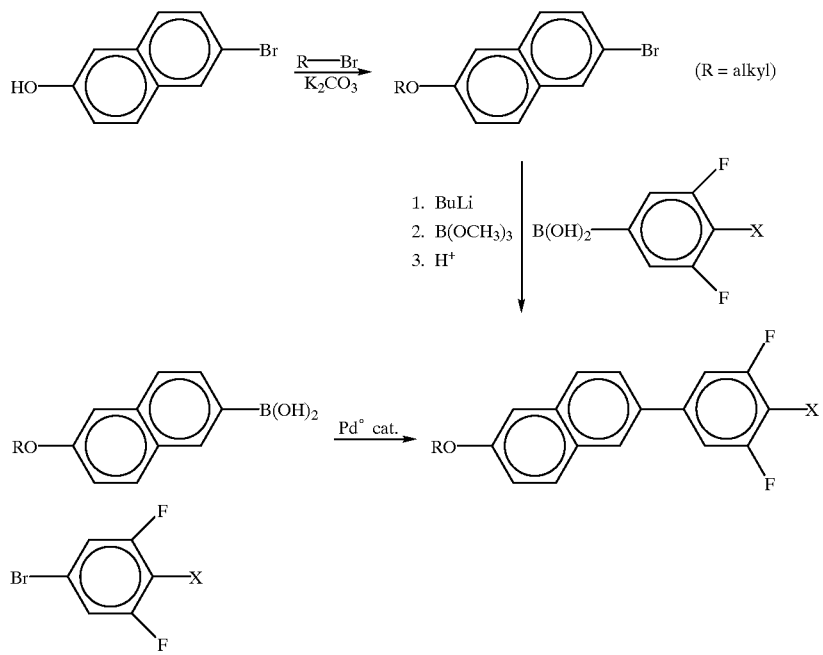

SCHEME 2
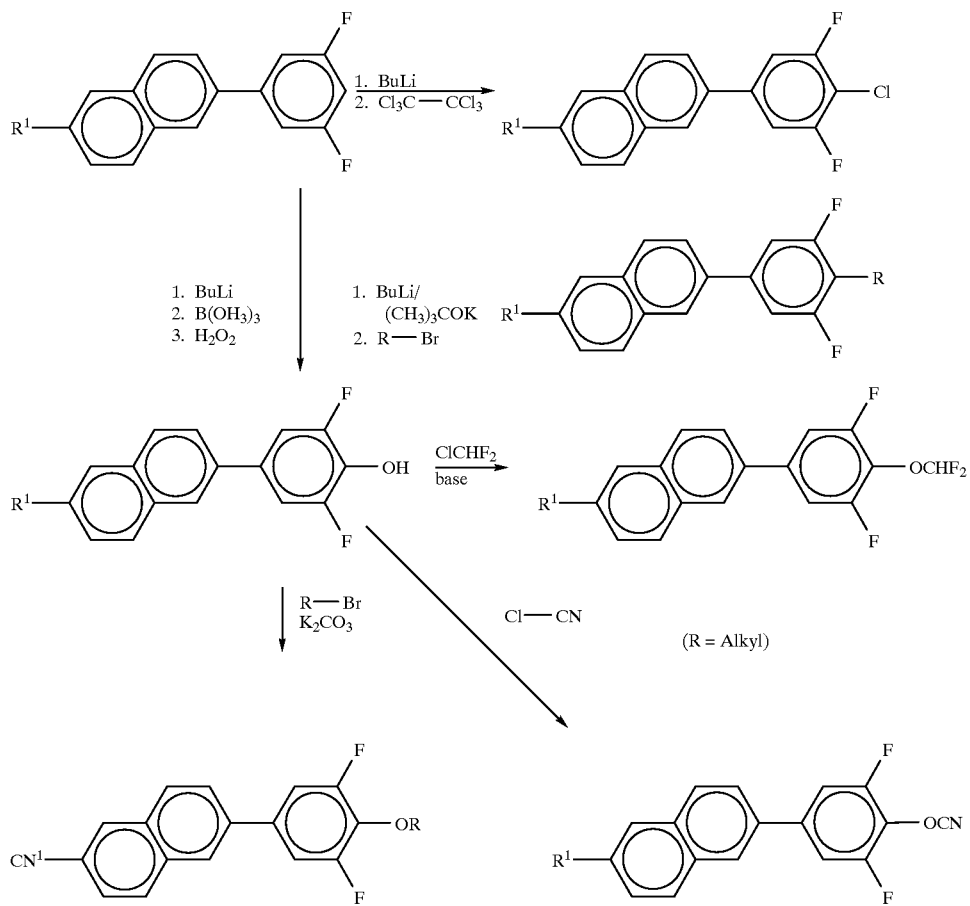
SCHEME 3
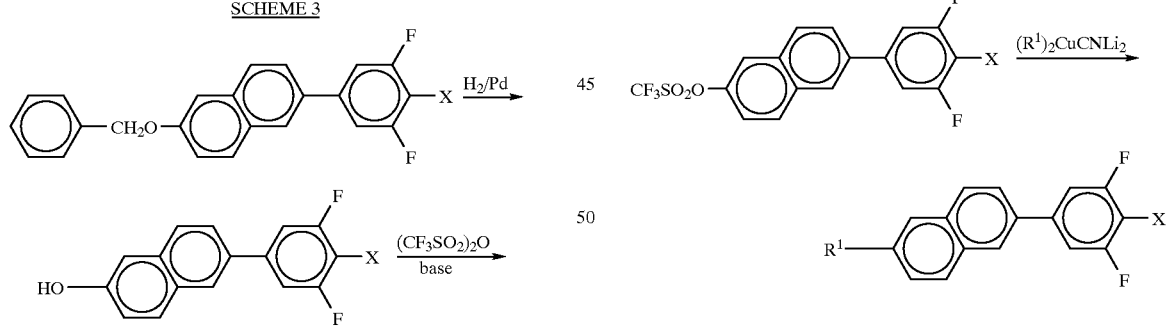

SCHEME 4
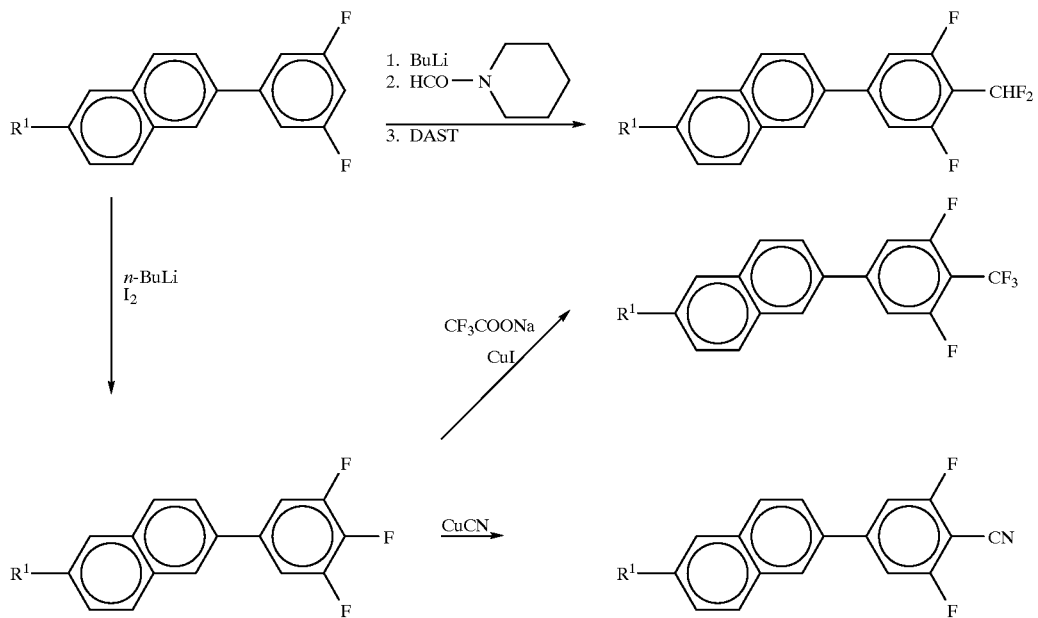
SCHEME 5
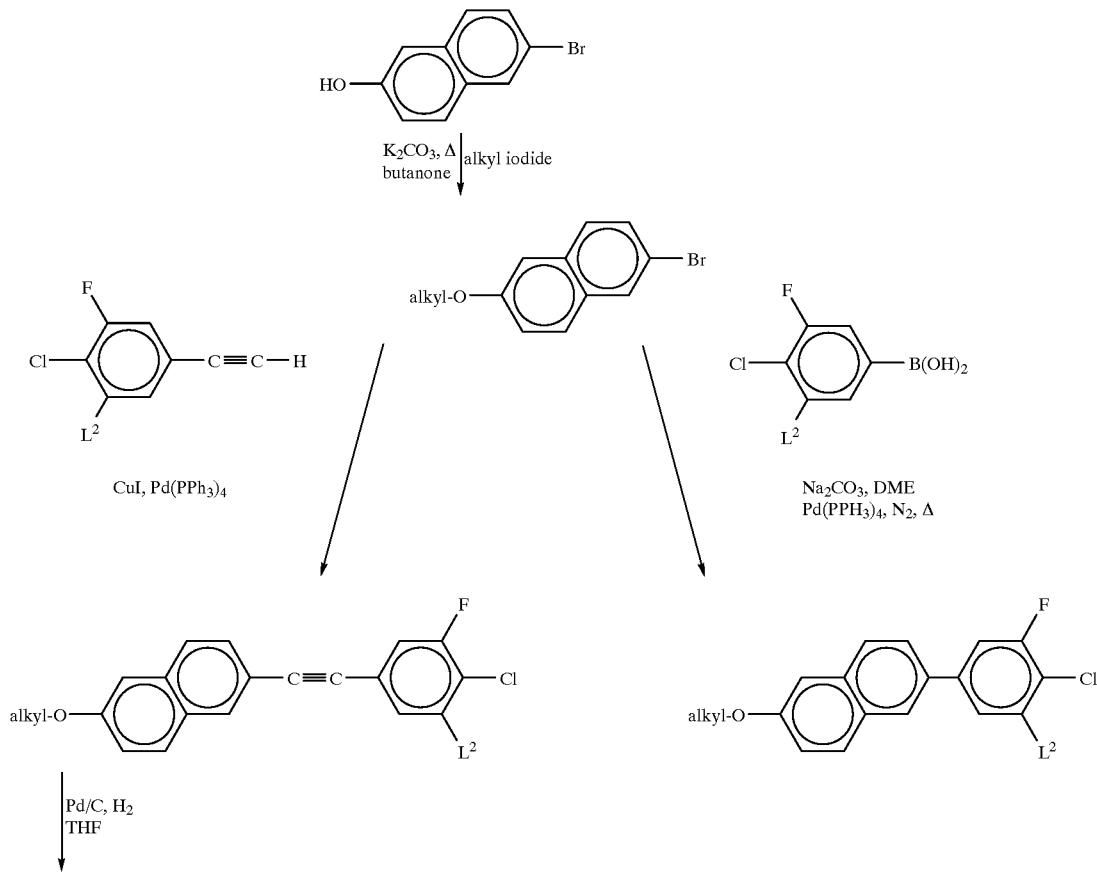

-continued
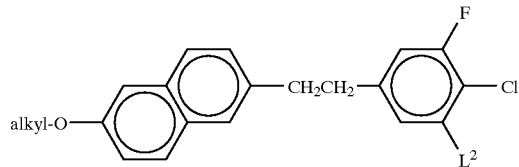
SCHEME 6
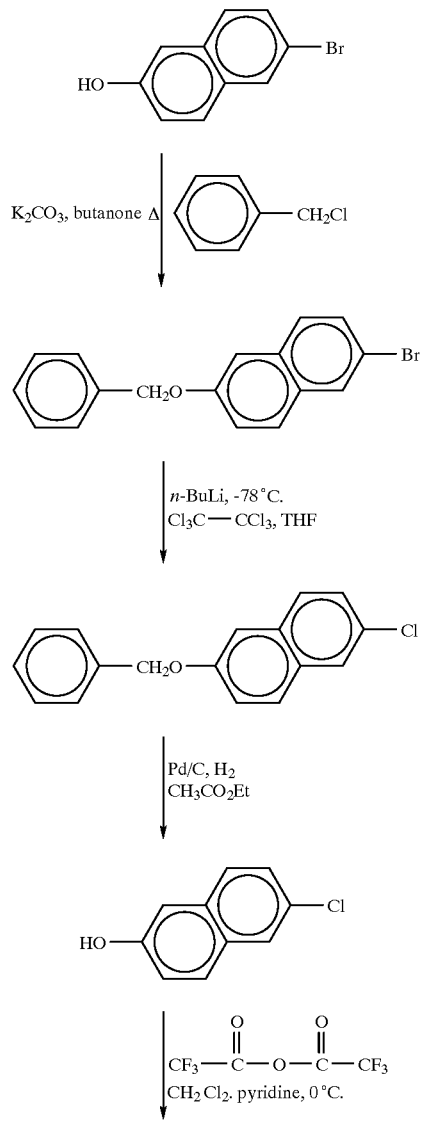

-continued

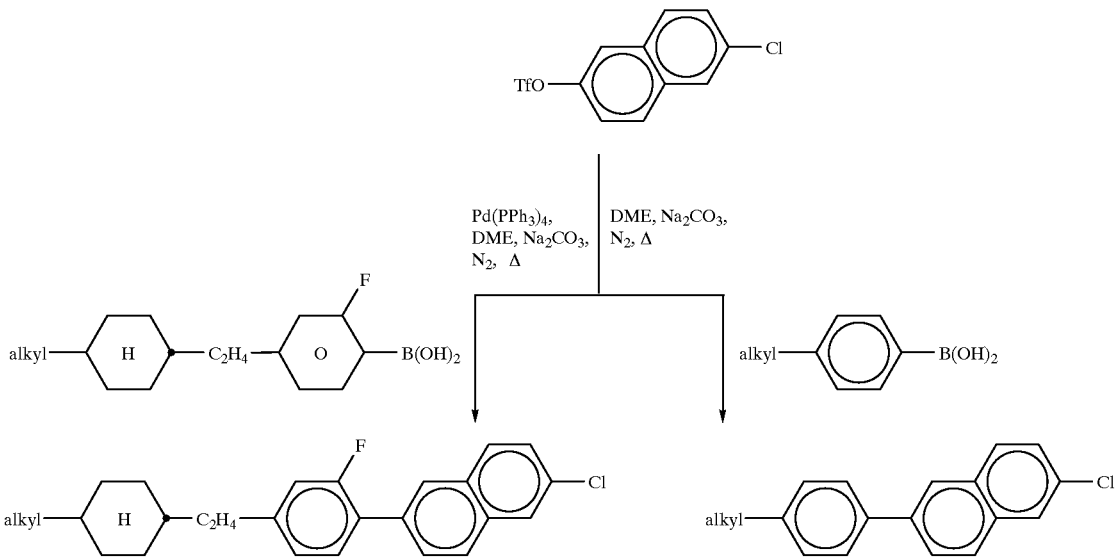

Other methods of synthesis are obvious to a person skilled in the art.

The starting materials are known or can be prepared analogously to known compounds.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenese benzylideneanilinese biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidinesa phenyl- or cyclohexylpyridinese phenyl- or cyclohexyldioxanese phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenese benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

R'-L-E-R" 1
R'-L-COO-E-R" 2
R'-L-OOC-E-R" 3
R'-L-CH$_2$CH$_2$-E-R" 4
R'-L-C≡C-E-R" 5

In the formulae 1 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is -CN, -CF$_3$, F, Cl or -NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The examples below are intended to illustrate the invention without representing a limitation. Above and below, percentages are percent by weight; all temperatures are indicated in degrees Celsius M.p. is melting point, c.p.= clearing point. Furthermore, C=crystalline state, N=nematic phase, S=smectic phase and I=isotropic phase. The numbers between these symbols indicate the transition temperatures. Δn denotes optical anisotropy (589 nm, 20° C.), and the viscosity (mm²/sec) was determined at 20° C.

"Customary work-up" means that water is added if necessary, the mixture is extracted with methylene chloride, diethyl ether or toluene, the organic phase is separated off, dried and evaporated, the product is purified by distillation under reduced pressure or crystallisation and/or chromatography. The following abbreviations are used:

| BuLi | butyllithium |
| DMS | dimethyl sulphate |
| THF | tetrahydrofuran |
| TTPP | tetrakis(triphenylphosphine)palladium(O) |

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples all temperatures are set forth in degrees Celsius; and, unless otherwise indicated, all parts and percentages are by weight.

The entire disclosures of all applications, patents, and publications cited herein, and of corresponding British Patent Application No. 9222178.7, filed Oct. 22, 1992, are hereby incorporated by reference.

EXAMPLES

Example 1

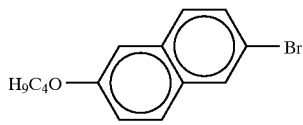

0.2 mol of 1-bromobutane in 100 ml of acetone are added dropwise to a refluxing mixture of 0.2 mol of 2-hydroxy-6-bromonaphthalene and 0.4 mol of potassium carbonate dissolved in 500 ml of acetone. The mixture is subsequently refluxed for 24 hours. The potassium carbonate is filtered off, and the mixture is subsequently subjected to customary work-up.

The following compounds are prepared analogously:

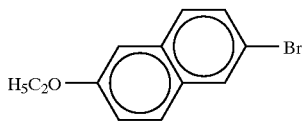

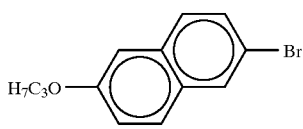

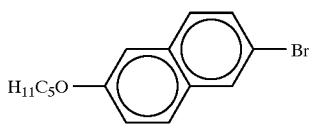

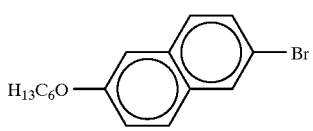

Example 2

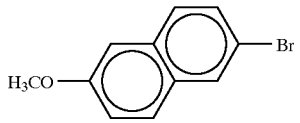

0.25 mol of DHS is added in portions to a stirred solution of 0.2 mol of 2-hydroxy-6-bromonaphthalene and 0.25 mol of potassium hydroxide in water. The mixture is stirred for one hour at 70° C. and subsequently overnight at room temperature. The mixture is then filtered, the filtrate is washed with 10% sodium hydroxide solution, and the mixture is subjected to customary work-up.

Example 3

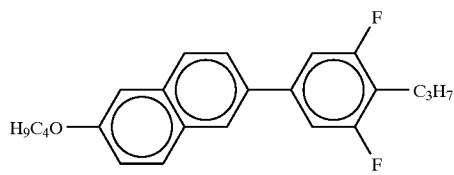

10 mmol of 2-butoxy-6-bromonaphthalene in 30 ml of ethanol are added dropwise under a nitrogen atmosphere to 14 mmol of 1-propyl-2,6-difluorophenylboric acid (prepared from 4-propyl-3,5-difluorobromobenzene using magnesium and trimethyl borate), 60 ml of 2M potassium carbonate solution and 0.5 mmol of TTPP in 60 ml of benzene. The mixture is refluxed for 24 hours and subsequently subjected to customary work-up.

The following novel compounds of the formula

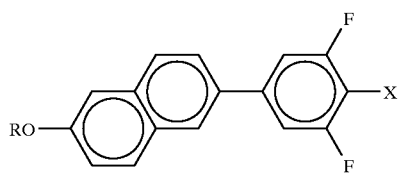

are obtained analogously from the corresponding precursors.

| R | X |
|---|---|
| $CH_3$ | $n-C_2H_5$ |
| $CH_3$ | $n-C_3H_7$ |
| $n-C_2H_5$ | $CH_3$ |
| $n-C_2H_5$ | $n-C_2H_5$ |
| $n-C_2H_5$ | $n-C_3H_7$ |
| $n-C_2H_5$ | $n-C_4H_9$ |
| $n-C_2H_5$ | $n-C_5H_{11}$ |
| $n-C_3H_7$ | $CH_3$ |
| $n-C_3H_7$ | $n-C_2H_5$ |
| $n-C_3H_7$ | $n-C_3H_7$ |
| $n-C_3H_7$ | $n-C_4H_9$ |
| $n-C_3H_7$ | $n-C_5H_{11}$ |
| $n-C_4H_9$ | $CH_3$ |
| $n-C_4H_9$ | $n-C_2H_5$ |
| $n-C_4H_9$ | $n-C_4H_9$ |
| $n-C_4H_9$ | $n-C_5H_{11}$ |

Example 4

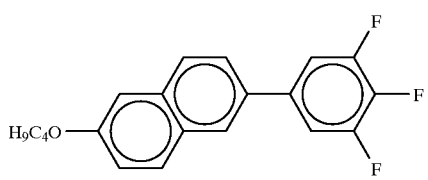

0.03 mol of n-BuLi (2.5M solution in hexane) is added dropwise under a nitrogen atmosphere to 0.03 mol of 2-bromo-6-butoxynaphthalene in 60 ml of THF. The mixture is subsequently stirred for 2.5 hours at −78° C. 0.064 mol of triisopropyl borate in 50 ml of THF is added, and the mixture is allowed to warm to room temperature overnight, then acidified using dilute HCl, stirred for a further hour and then subjected to customary work-up 7.10 mmol of 1-bromo-3,4,5-trifluorobenzene, 0.23 mmol of TTPP, 2M of potassium carbonate solution in 30 ml of benzene are added to 9.30 mmol of the crude product, and the mixture is refluxed for 24 hours and then subjected to customary work-up.

The following compounds of the formula

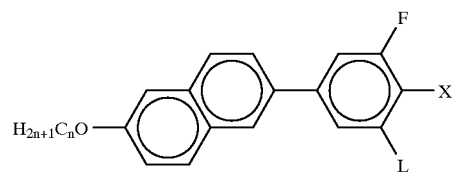

are prepared analogously from the corresponding starting materials:

| n | X | L |
|---|---|---|
| 1 | F | F |
| 1 | Cl | F |
| 1 | Cl | H |
| 2 | F | F |
| 2 | Cl | F |
| 2 | Cl | H |
| 3 | F | F |
| 3 | Cl | F |
| 3 | Cl | H |
| 3 | CN | F |
| 4 | Cl | F |
| 4 | Cl | H |
| 5 | F | F |
| 5 | Cl | F |
| 5 | Cl | H |
| 5 | CN | F |

Example 5

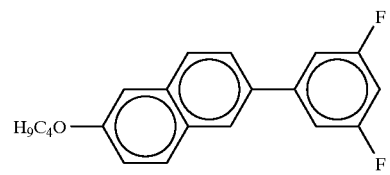

7.0 mmol of 3,5-difluaorophenylboric acid are reacted with 5.2 mmol of 2-butoxy-6-bromohaphthalene analogously to Example 2. The following compounds are obtained analogously from the corresponding precursors:

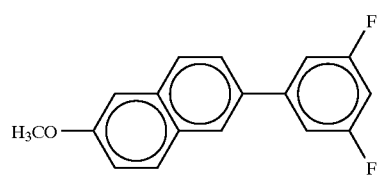

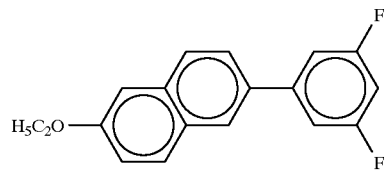

-continued

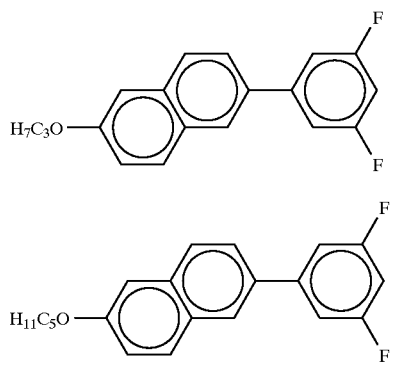

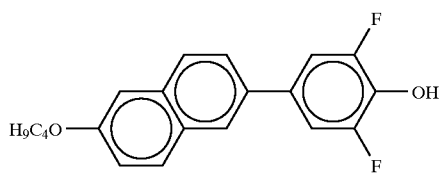

Example 6

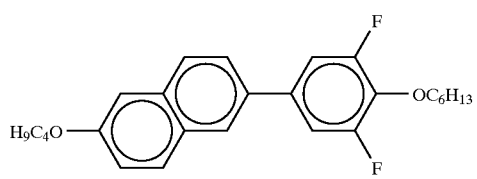

26 mmol of n-BuLi are added dropwise at −70° C. to a mixture comprising 26 mmol of 3,5-difluorophenyl-6-butoxynaphthalene from Example 5 and 60 ml of THF. After the mixture has been stirred at −70° C. for one hour, 36 mmol of trimethyl borate are added dropwise at the same temperature. The mixture is stirred for a further 0.05 hour, and 42 mmol of acetic acid are then added dropwise at −20° C. The mixture is subsequently warmed to 30° C. 4.2 mmol of $H_2O_2$ are added dropwise at this temperature, and the mixture is stirred for two hours at from 50 to 60° C. The mixture is cooled to room temperature, and a 5% sodium dithionate solution is added. Phase separation and customary work-up give the difluorophenol derivative Example 7

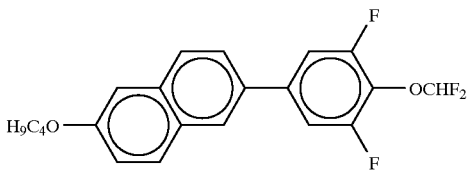

The product obtained in Example 6 is reacted with hexyl iodide in acetone under reflux in the presence of potassium carbonate to give the hexyl ether. Customary work-up and chromatography on silica gel using hexane give the ether in pure form.

The following compounds of the formula

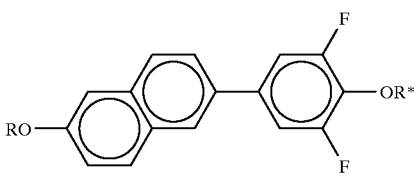

are obtained analogously from the corresponding precursors.

| R | R* |
| --- | --- |
| $CH_3$ | $CH_3$ |
| $CH_3$ | $C_2H_5$ |
| $CH_3$ | $C_3H_7$ |
| n-$C_2H_5$ | $CH_3$ |
| n-$C_2H_5$ | $C_2H_5$ |
| n-$C_2H_5$ | n-$C_3H_7$ |
| n-$C_2H_5$ | n-$C_4H_9$ |
| n-$C_2H_5$ | n-$C_5H_{11}$ |
| n-$C_3H_7$ | $CH_3$ |
| n-$C_2H_5$ | $C_2H_5$ |
| n-$C_2H_5$ | n-$C_3H_7$ |
| n-$C_2H_5$ | n-$C_4H_9$ |
| n-$C_2H_5$ | n-$C_5H_{11}$ |
| n-$C_2H_5$ | n-$C_6H_{13}$ |
| n-$C_4H_9$ | $CH_3$ |
| n-$C_4H_9$ | $C_2H_5$ |
| n-$C_4H_9$ | n-$C_3H_7$ |
| n-$C_4H_9$ | n-$C_4H_9$ |
| n-$C_4H_9$ | n-$C_5H_{11}$ |
| n-$C_5H_{11}$ | $C_2H_5$ |
| n-$C_5H_{11}$ | n-$C_3H_7$ |
| n-$C_5H_{11}$ | n-$C_4H_9$ |
| n-$C_5H_{11}$ | n-$C_5H_{11}$ |
| n-$C_5H_{11}$ | n-$C_6H_{13}$ |

Example 8

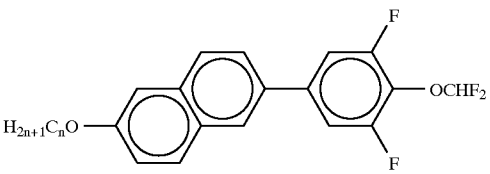

3.1 g of a 32% sodium hydroxide solution and 0.5 g of tetrabutylammonium hydrogen sulphate are added to 0.01 mol of the difluorophenol derivative from Example 6 in THF, and the mixture is warmed to 50° C. Chlorodifluoromethane is added to the stirred mixture until it condenses on a condenser cooled by means of dry ice. After cooling, the THF solution is filtered The mixture is subsequently subjected to customary work-up.

The following compounds of the formula

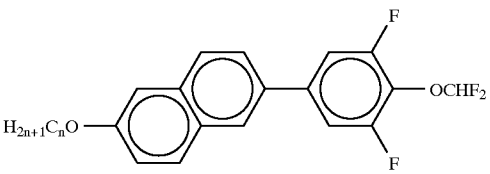

are prepared analogously from the corresponding precursors.

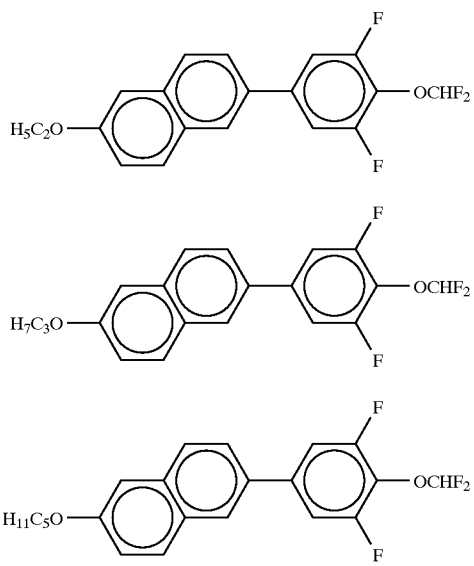

Example 9

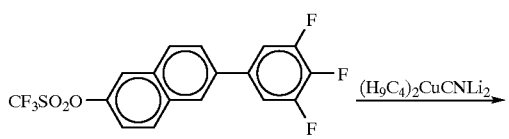

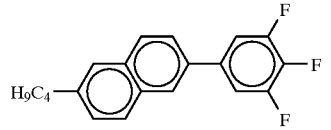

0.1 mol of BuLi (in the form of a 15% solution in n-haxane) is added dropwise at −70° C. to a suspension of 0.05 mol of CuCN in 100 ml of THF, and the mixture is then allowed briefly to warm to −20° C. A solution of 0.02 mol of the triflate in THF is then added dropwise at −70° C. the mixture is then allowed to warm to −20° C. and is subsequently stirred at this temperature for 6 hours, hydrolysed and subjected to customary work-up.

The following compounds of the formula

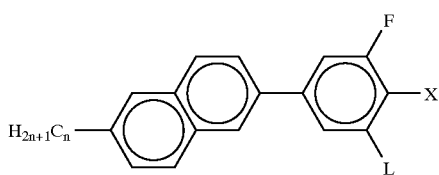

are prepared analogously from the correspoinding starting compounds:

| n | X | L |
|---|---|---|
| 2 | $CH_3$ | F |
| 2 | $C_2H_5$ | F |
| 2 | n-$C_3H_7$ | F |

-continued

| n | X | L |
|---|---|---|
| 2 | n-$C_4H_9$ | F |
| 2 | n-$C_5H_9$ | F |
| 2 | $OC_2H_5$ | F |
| 2 | $OC_3H_7$ | F |
| 2 | $OC_4H_9$ | F |
| 2 | F | F |
| 2 | Cl | H |
| 2 | Cl | F |
| 2 | CN | F |
| 2 | OH | H |
| 2 | OH | F |
| 2 | $OCF_3$ | F |
| 2 | $OCHF_2$ | F |
| 2 | $OCH_2F$ | H |
| 2 | $CF_3$ | F |
| 2 | $CHF_2$ | F |
| 3 | F | F |
| 3 | Cl | H |
| 3 | Cl | F |
| 3 | OH | H |
| 3 | OH | F |
| 3 | CN | F |
| 3 | $CF_3$ | F |
| 3 | $OCF_3$ | F |
| 3 | $CHF_2$ | F |
| 3 | $CH_2F$ | F |
| 3 | $OCHF_2$ | F |
| 3 | $OCH_2F$ | F |
| 4 | Cl | H |
| 4 | Cl | F |
| 4 | OH | H |
| 4 | OH | F |
| 4 | CN | F |
| 4 | $CF_3$ | F |
| 4 | $OCF_3$ | F |

Example 10

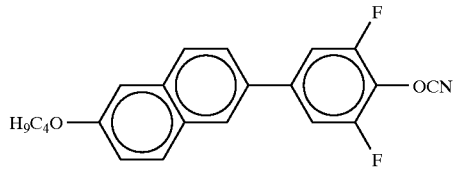

0,1 mol of the difluorophenol derivative obtained in Example 6 is reacted with 0,105 mol of cyanogen chloride at 0° C.

The mixture is stirred at 0° C. and 0,1 mol of triethylamine are added dropwise at the same temperature. Phase separation and customary work-up give the desired product.

The following compounds are obtained analogously from the corresponding precursors.

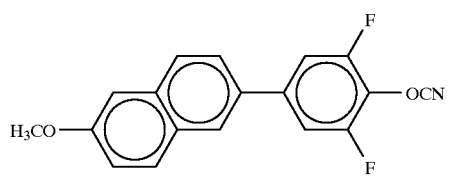

-continued

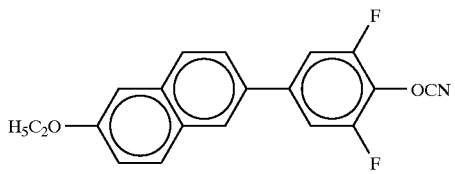

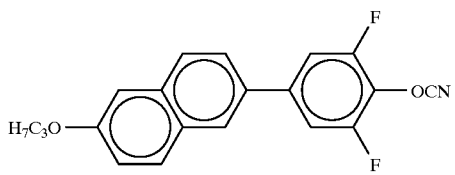

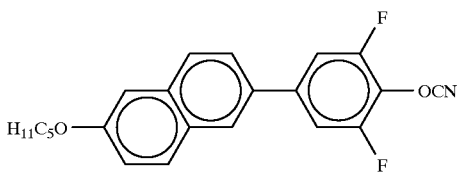

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A naphthalene derivative of the formula I

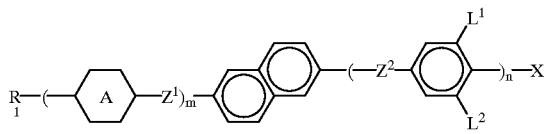

in which $R^1$ is an alkyl or alkenyl radical which is unsubstituted, monosubstituted by CN or $CF_3$ or substituted by halogen and has 1 to 15 carbon atoms, it also being possible for one or more $CH_2$ groups in these radicals to be replaced, in each case independently of one another, by -O-, -S-,

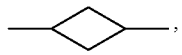

-CO-, -CO- O-, -O-CO- or -OCO-O- in such a manner that oxygen atoms are not linked directly to one another,

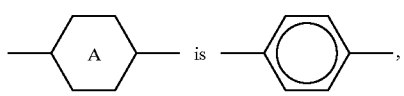

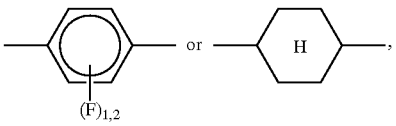

m is 1 or 2 or
n is 0 or 1, and
m+n is 2,
$Z^1$ and $Z^2$ are each, independently of one another, -$CH_2CH_2$-, -C≡C- or a single bond,
$L^1$ and $L^2$ independently of one another, are H or F,
X is an alkyl or alkoxy radical which is unsubstituted, monosubstituted by CN or $CF_3$ or substituted by halogen and has 1 to 15 carbon atoms, or is OH, CN, SCN, OCN, NCS or Q—Y,
where Q is a single bond, $(CF_2)$, or $O(CF_2)_r$,
r is 1 or 2, and
Y is H, F, Cl or Br.

2. A compound of the formula

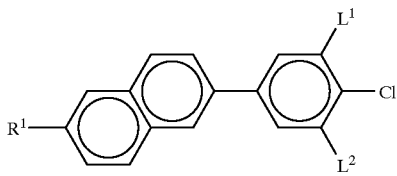

in which $R^1$ is an alkyl or alkenyl radical which is unsubstituted, monosubstituted by CN or $CF_3$ or substituted by halogen and has 1 to 15 carbon atoms, it also being possible for one or more $CH_2$ groups in these radicals to be replaced in each case independently of one another, by -O-, -S-,

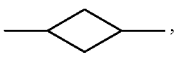

-CO-, -CO- O-, -O-CO- or -OCO-O- in such a manner that oxygen atoms are not linked directly to one another, and
$L^1$ and $L^2$ are independently of one another, H or F.

3. A compound of the formula

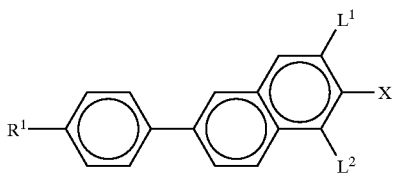

in which $R^1$ is an alkyl or alkenyl radical which is unsubstituted, monosubstituted by CN or $CF_3$ or substituted by halogen and has 1 to 15 carbon atoms, it also being possible for one or more $CH_2$ groups in these radicls to be replaced in each case independently of one another, by -O-, -S-,

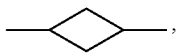

-CO-, -CO- O-, -O-CO- or -OCO-O- in such a manner that oxygen atoms are not linked directly to one another, X is an alkyl or alkoxy radical which is unsubstituted, monosubstituted by CN or CF$_3$ or substituted by halogen and has 1 to 15 carbon atoms, or is OH, CN, SCN, OCN, NCS or Q-Y.

L$^1$ and L$^2$ are independently of one another, are H or F and

Q is a single bond, (CF$_2$)$_n$ or O(CF$_2$)$_r$, r is 1 or 2, and

Y is H, F, Cl or Br.

4. A compound of the formula

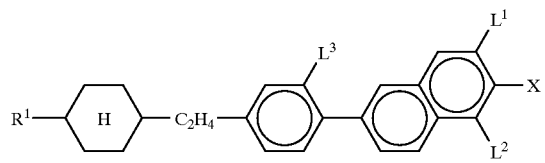

in which

R$^1$ is an alkyl or alkenyl radical which is unsubstituted monosubstituted by CN or CF$_3$ or substituted by halogen and has 1 to 15 carbon atoms, it also being possible for one or more CH$_2$ groups in these radicals to be replaced in each case independently of one another, by -O-, -S-,

-CO-, -CO- O-, -O-CO- or -OCO-O- in such a manner that oxygen atoms are not linked directly to one another, X is an alkyl or alkoxy radical which is unsubstituted monosubstituted by CN or CF$_3$ or substituted by halogen and has 1 to 15 carbon atoms or is OH, CN, SCN, OCN, NCS or Q-Y, L$^1$ and L$^2$ are independently of one another, H or F, L$^3$ is H or F, and Q is a single bond, (CF$_2$)$_n$ or O(CF$_2$)$_r$, r is 1 or 2, and Y is H, F, Cl or Br.

* * * * *